(12) United States Patent
Isobe et al.

(10) Patent No.: US 7,459,123 B2
(45) Date of Patent: Dec. 2, 2008

(54) AUTOMATIC ANALYZER

(75) Inventors: Tetsuya Isobe, Hitachinaka (JP);
Katsuaki Takahashi, Hitachinaka (JP);
Masaharu Nishida, Hitachinaka (JP)

(73) Assignees: Hitachi High-Technologies Corporation, Tokyo (JP); Hitachi Science Systems, Inc., Ibaraki (JP)

( * ) Notice: Subject to any disclaimer, the term of this patent is extended or adjusted under 35 U.S.C. 154(b) by 576 days.

(21) Appl. No.: 11/012,291

(22) Filed: Dec. 16, 2004

(65) Prior Publication Data

US 2005/0135967 A1    Jun. 23, 2005

(30) Foreign Application Priority Data

Dec. 19, 2003  (JP) ............... 2003-421781

(51) Int. Cl.
*G01N 21/05* (2006.01)
*G01N 21/76* (2006.01)

(52) U.S. Cl. ............... 422/52; 422/68.1; 422/82.05; 422/101; 96/155

(58) Field of Classification Search ........... 422/50–104; 436/43–49; 96/155
See application file for complete search history.

(56) References Cited

U.S. PATENT DOCUMENTS

| | | | | |
|---|---|---|---|---|
| 3,592,605 | A | * | 7/1971 | Noma et al. ............... 422/64 |
| 4,209,131 | A | * | 6/1980 | Barash et al. ............ 239/68 |
| 4,804,519 | A | * | 2/1989 | Sainz et al. ............. 422/81 |
| 4,806,135 | A | * | 2/1989 | Siposs ................... 96/212 |
| 4,869,093 | A | * | 9/1989 | Gilbert ................. 73/23.35 |

FOREIGN PATENT DOCUMENTS

| | | |
|---|---|---|
| EP | 57208433 | 12/1982 |
| EP | 63085334 | 4/1988 |
| EP | 63165761 | 7/1988 |

(Continued)

OTHER PUBLICATIONS

"Improved Impinger Air Sampling Method by Using Highly Hydrophilic Surface and its Application Automatic Monitor for Acidic or Basic Contaminations in Cleanroom Air", U. Hase et al, Japan Association of Aerosol Science and Technology, vol. 19, No. 2 (2002), pp. 83-88.

*Primary Examiner*—Jill Warden
*Assistant Examiner*—Cedric A Chan
(74) *Attorney, Agent, or Firm*—Mattingly, Stanger, Malur & Brundidge, PC

(57) ABSTRACT

An automatic analyzer which can remove air bubbles in a photometric light path within a reaction tank and can provide accurate measurement results with stability. The automatic analyzer comprises a reaction cell for mixing a sample and a reagent therein, a constant temperature bath for holding water in which the reaction cell is immersed, a suction pipe for sucking the water in the constant temperature bath, a return pipe for returning the water to the constant temperature bath, a pump disposed between the suction pipe and the return pipe and circulating the water, a heater for heating the water circulated in the constant temperature bath by the pump, and an air-bubble removing unit disposed between the suction pipe and the return pipe, having a water-tight structure to hold the constant temperature bath water therein, and removing air bubbles based on a difference in gravity between the water and the air bubbles.

8 Claims, 3 Drawing Sheets

FOREIGN PATENT DOCUMENTS

| | | |
|---|---|---|
| EP | 10282108 | 10/1998 |
| JP | 58-74161 | 5/1983 |
| JP | 58074161 | 5/1983 |
| JP | 59-182368 | 10/1984 |
| JP | 10-282108 | 10/1998 |
| JP | 2000-039427 | 2/2000 |

* cited by examiner

AUTOMATIC ANALYZER

BACKGROUND OF THE INVENTION

1. Field of the Invention

The present invention relates to an automatic analyzer for performing qualitative and quantitative analyses of biological samples, such as blood and urine, and more particularly to an automatic analyzer provided with a constant temperature bath for holding reaction cells at a certain temperature.

2. Description of the Related Art

An automatic analyzer capable of performing qualitative and quantitative analyses of target components in samples in a short time with high accuracy is employed in widespread fields, primarily in inspection centers and large-scaled hospitals which are required to analyze a large number of samples in a short time. The principle of such an automatic analyzer resides in utilizing a reagent which reacts with the target component and causes a chemical change, and analyzing a degree of the chemical change by using a photometer or the like.

To maintain the reaction condition between the sample and the reagent constant for an improvement of measurement accuracy, the automatic analyzer generally has a structure that reaction cells are immersed in constant temperature water held at a certain temperature.

The constant temperature water is circulated while being heated by a heater or the like so that the water is kept at a certain temperature (e.g., about 37° C.). In such a system, however, air bubbles may often mix in and circulate with the constant temperature water.

When those air bubbles attach to the surfaces of the reaction cells, they may impede the photometry made by the photometer. To avoid such a trouble, Patent Reference 1: JP,A 10-282108 discloses a method of removing air bubbles through the steps of (1) when water circulating in a constant temperature bath is drained, draining a certain amount of the circulating water instead of draining all of the circulating water, (2) providing a water supply port such that pure water is delivered in a direction to strike against an inner wall of the constant temperature bath, thereby causing the air bubbles in the water to rise to the water surface, and (3) adding a surfactant into the constant temperature bath and rotating a reaction disk, to which reaction cells are mounted, in one direction or in forward and backward directions so as to carry away the air bubbles. Also, Patent Reference 2: JP,U 58-74161 discloses a method of washing away air bubbles attached to the surface of a reaction cell by throttling a flow of water in a constant temperature bath near the reaction cell so as to increase the flow speed of the water in the constant temperature bath.

SUMMARY OF THE INVENTION

The inventions disclosed in the above-cited Patent References 1 and 2 are both intended to remove air bubbles by carrying or washing away the air bubbles from the reaction cell surface. However, those methods have a difficulty in removing fine air bubbles that are formed by, e.g., oxygen dissolved in the circulating water upon heating with a heater. Also, a channel in the constant temperature bath is branched into a main channel for keeping the reaction cell at the certain temperature and a sub-channel for cooling a lamp of the photometer, etc., and air bubbles accumulated in a lamp cooling pipe, etc. enter the main channel a little by a little. The known control methods are able to remove the air bubbles generated in an initial stage, e.g., at the time of exchange of the circulating water, but air bubbles generated during the analyzer operation are very difficult to remove with those methods. Meanwhile, reducing an amount of reaction liquid is demanded. Correspondingly, there is a tendency to increase the intensity of light emitted from the photometer lamp so that a measurement result comparable to a current level can be obtained with a smaller amount of reaction liquid. Such a case raises a possibility that even those fine air bubbles, which have been free from problems in the past, may affect the measurement result.

Accordingly, it is an object of the present invention to provide an automatic analyzer, which can remove not only fine air bubbles in water within a constant temperature bath, but also air bubbles generated during the analyzer operation, and which can realize stable analysis.

To achieve the above object, the present invention is constructed as follows.

The automatic analyzer comprises a reaction cell for mixing a sample and a reagent therein, a constant temperature bath for holding water in which the reaction cell is immersed, a suction pipe for sucking the water in the constant temperature bath, a return pipe for returning the water to the constant temperature bath, a pump disposed between the suction pipe and the return pipe and circulating the water, a heater for heating the water circulated in the constant temperature bath by the pump, and an air-bubble removing unit disposed between the suction pipe and the return pipe, having a water-tight structure to hold the constant temperature bath water therein, and removing air bubbles based on a difference in gravity between the water and the air bubbles.

The expression "reaction cell for mixing a sample and a reagent therein" means a reaction cell capable of mixing a sample and a reagent therein, and it does not always require a mechanism for positively mixing a mixture. The expression "the reaction cell is immersed" means a state in which at least a part of the reaction cell is immersed in the water. The reaction cell is not always required to be entirely immersed in the water. In other words, it is essential that the reaction cell be immersed in the water in such a state as enabling the reaction cell to be kept at a certain temperature.

Usually, the temperature of the water in the constant temperature bath is controlled such that the reaction in the reaction cell takes place at a certain temperature (e.g., 37° C.). The heater is used to maintain the water temperature constant. More specifically, the water in the constant temperature bath is kept at the certain temperature through the steps of sucking the water in the constant temperature bath, controlling the water temperature by the heater, and returning the water having the controlled temperature to the constant temperature bath.

Since the air-bubble removing unit has a structure of removing the air bubbles based on a difference in gravity between the water and the air bubbles, it is preferable that a pipe joint position of the air-bubble removing unit on the side connected to the suction pipe be higher than a pipe joint position of the air-bubble removing unit on the side connected to the return pipe (i.e., higher than that in the direction of action of gravity).

According to the present invention, in an automatic analyzer employing a constant temperature bath of warm-water circulating type to hold a row of reactions cells at a certain temperature, air bubbles in a photometric light path of a photometer within a reaction tank are perfectly removed, and therefore accurate measurement results can be obtained with stability.

DESCRIPTION OF THE PREFERRED EMBODIMENTS

Embodiments of the present invention will be described below with reference to the drawings.

Embodiment 1

Figure 1:
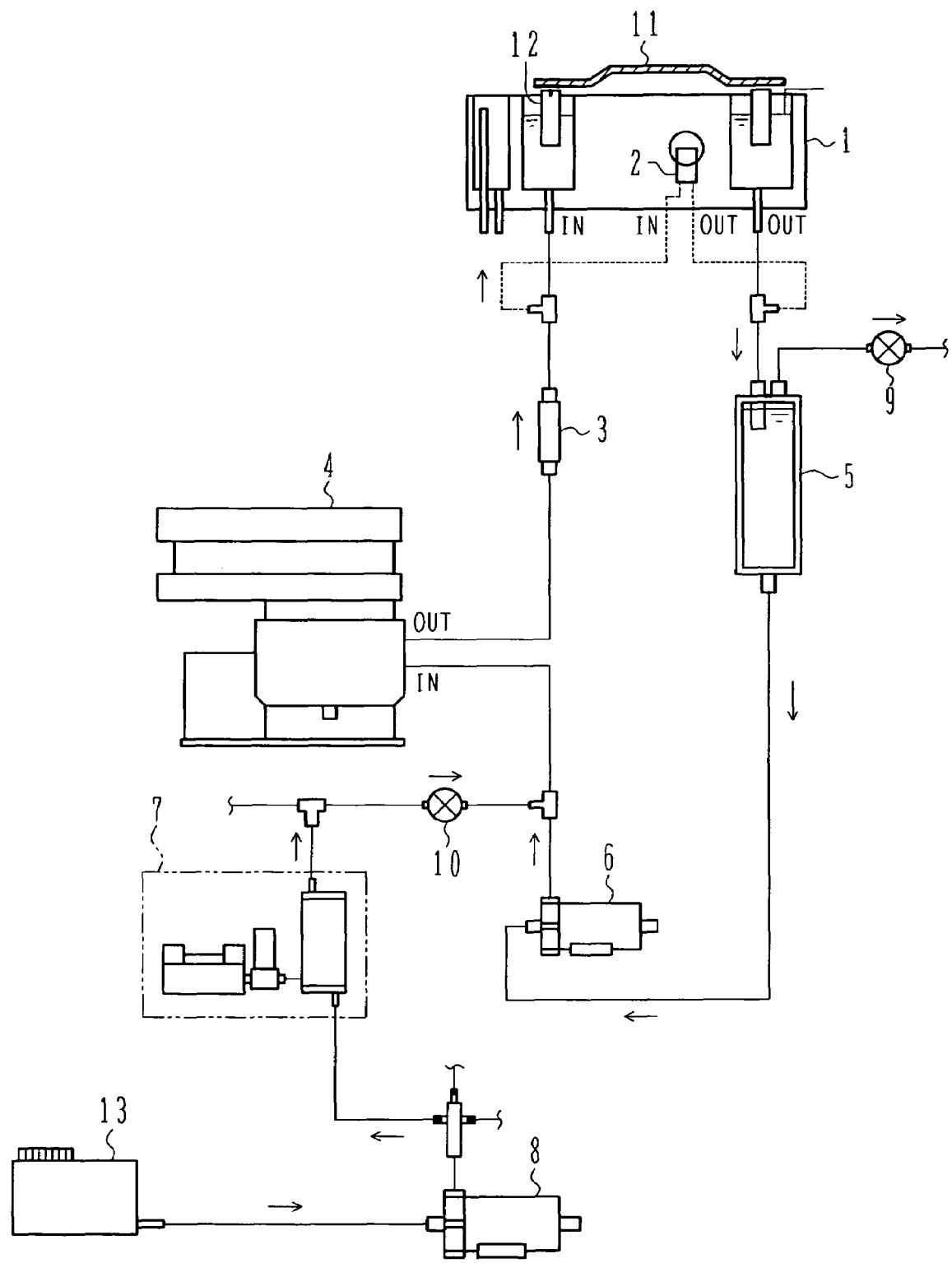
FIG. 1 is a schematic view of an automatic analyzer employing an air-bubble removing unit according to the present invention.

FIG. 1 is a schematic view showing a constant temperature bath of warm-water circulating type used in an automatic analyzer. To keep a sample and a reagent in each of reaction cells 12 mounted to a reaction table 11 at about 37° C., water in the constant temperature bath 1 (hereinafter referred to as "constant temperature bath water") is held at a temperature of about 37° C. with on/off control of a heater 3. The automatic analyzer further comprises a circulation pump 6 for circulating the constant temperature bath water, a reagent cooling unit 4 for keeping cool reagents and for cooling the circulating water when the water temperature rises excessively, a pipe 2 used for cooling a photometer lamp, a solenoid valve 10 for water supply, a trap 5 for removing air bubbles (hereinafter also referred to as an "air-bubble removing unit"), and a solenoid valve 9 for water drain. Further, a water supply pump 8 for supplying water to the constant temperature bath and a degassing unit 7 for removing oxygen dissolved in the supplied water are both connected to the constant temperature bath. The water to be supplied is stored in a water supply tank 13. A light emitted from the photometer lamp is illuminated to a mixture of the sample and the reagent in the reaction cell, and the light having passed through the mixture is measured by the photometer, thereby performing qualitative and quantitative analyses of a particular component in the sample.

If a large amount of air bubbles are present in the constant temperature bath, such a condition leads to a possibility that air bubbles may attach to the reaction cell surface. Then, the attached air bubbles possibly cause diffused reflection of the light emitted from the photometer lamp and reduce the measurement accuracy.

A first stage of a method for removing air bubbles can be performed at the time of exchanging the circulating water in the constant temperature bath. In other words, air bubbles contained in the water supplied to the constant temperature bath are removed when the water passes through the degassing unit 7.

However, there is a risk that air bubbles having accumulated in the lamp cooling pipe 2 during circulation of the constant temperature bath water flow away a little by a little, or air bubbles are caught into the water near the water surface of the constant temperature bath because of a structure being open to the atmosphere. The air-bubble removing unit (trap) 5 is employed to remove those air bubbles. The trap 5 is in the form of a long tube and is able to store a certain amount of water without leaking. When the water including air bubbles enters the trap 5, the air bubbles accumulate in an upper portion of the trap 5 due to a difference in gravity between the air bubbles and the water. Then, only the water is returned to the circulation pump 6 from the bottom of the trap 5. The air bubbles accumulated in the trap 5 can be expelled out of the analyzer through the water drain solenoid valve 9. For example, by incorporating software program in the analyzer so as to open the water drain solenoid valve 9 at intervals of a certain time, the air bubbles accumulated during the analyzer operation can be automatically expelled out to the exterior.

Embodiment 2

Figure 2:
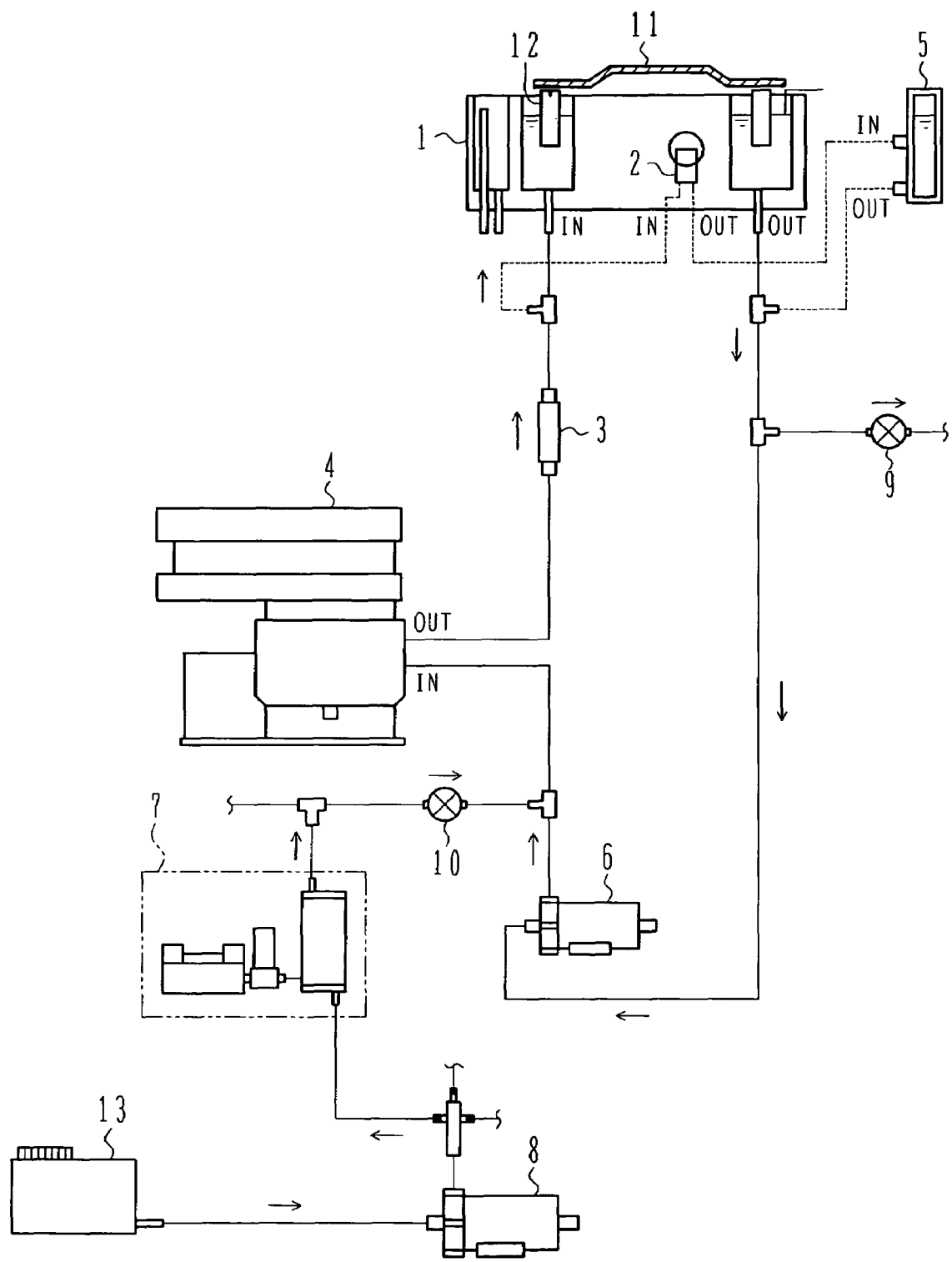
FIG. 2 is a schematic view of an automatic analyzer employing another air-bubble removing unit according to the present invention.

FIG. 2 is a schematic view of another embodiment in which the trap 5 is provided in a sub-channel. The trap 5 is provided to locate at the same level as the water surface in the reaction tank 1, and the top of the trap 5 is left open to the atmosphere. With such an arrangement, air bubbles accumulated in the trap 5 is naturally released out of the analyzer.

Figure 3A:
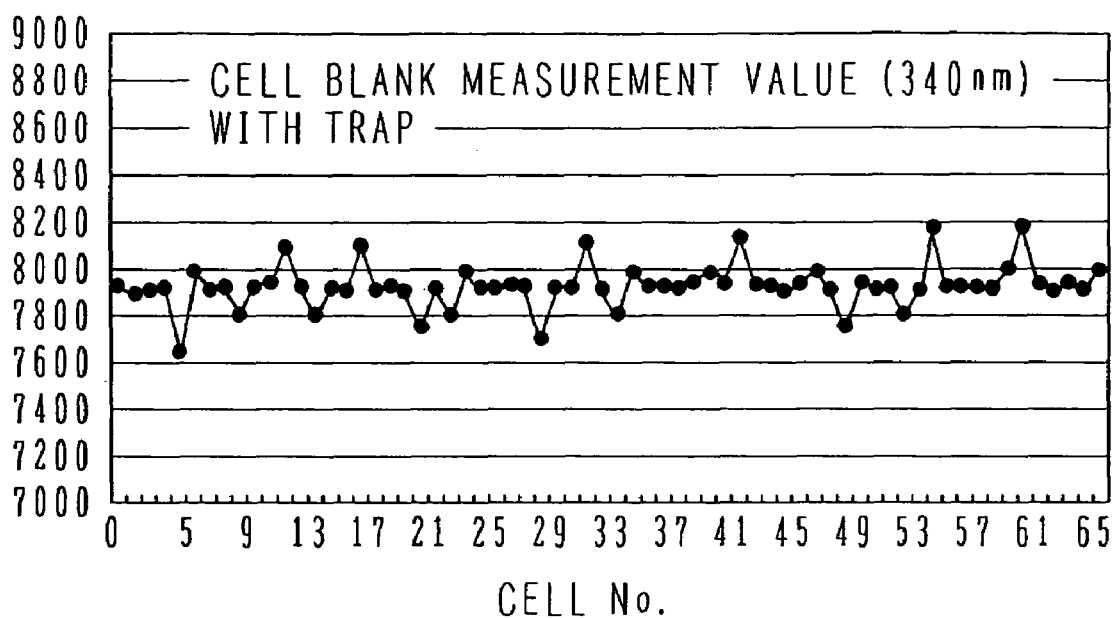
FIGS. 3A and 3B are graphs showing variations of measured values depending on the presence or absence of the air-bubble removing unit according to the present invention.
Figure 3B:
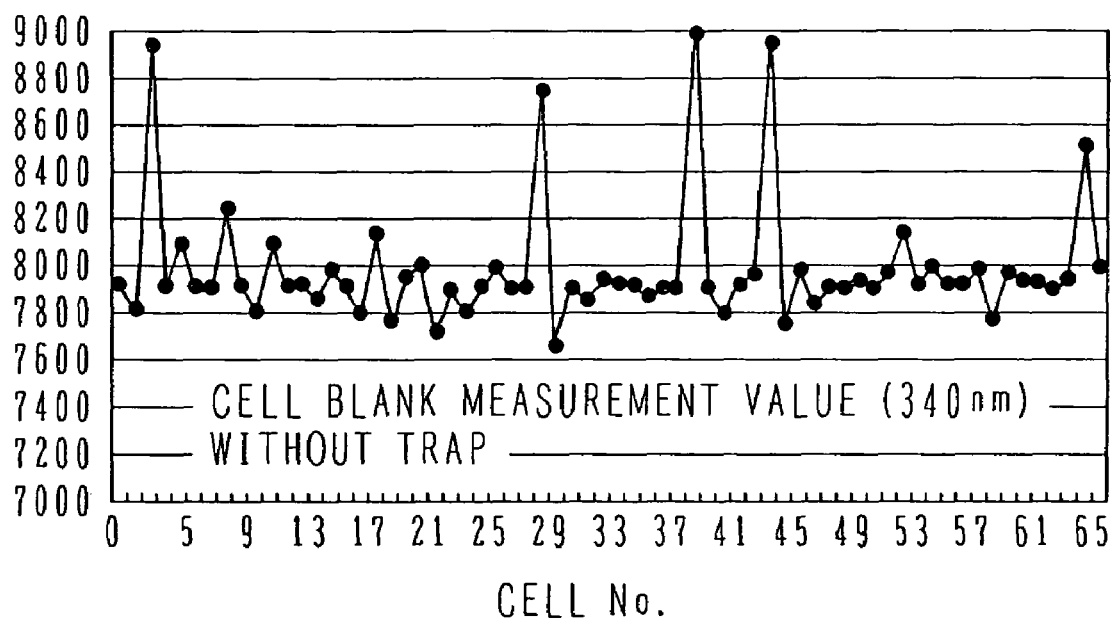

FIGS. 3A and 3B show comparative data of measurement results obtained with cell blank measurement (in which the measurement is performed by putting water, instead of a sample, in the reaction cell for calibration of values measured by the photometer) when the trap 5 is provided and when it is not provided. The vertical axis represents absorbance, and the horizontal axis represents the position number of each reaction cell (container) mounted to the reaction disk. As seen, when the trap 5 is not provided, the cell blank measured value varies depending on the cell position. This is presumably attributable to the fact that the air bubbles attached to the reaction cell surface, etc. cause diffused reflection of the light emitted from the photometer lamp. On the other hand, when the trap (air-bubble removing unit) 5 is provided, variations of the cell blank measured value are suppressed to be comparatively small. Thus, the provision of the air-bubble removing unit makes it possible to obtain measured values with more stability.

What is claimed is:

1. An automatic analyzer comprising:
    a reaction cell for mixing a sample and a reagent therein;
    a constant temperature bath for holding water in which said reaction cell is immersed;
    a photometer for measuring target components in a sample;
    a suction pipe for sucking the water in said constant temperature bath;
    a return pipe for returning the water to said constant temperature bath;
    a pump disposed between said suction pipe and said return pipe and circulating the water;
    a heater for heating the water circulated in said constant temperature bath by said pump;
    a sub-channel for cooling a lamp of said photometer, said sub-channel disposed between said suction pipe and said return pipe; and
    an air-bubble removing unit disposed at said sub-channel, having a water-tight structure to hold the constant temperature bath water therein, and removing air bubbles based on a difference in specific gravity between the water and the air bubbles.

2. An automatic analyzer according to claim 1, wherein a pipe joint position of said air-bubble removing unit on the side connected to said suction pipe is higher than a pipe joint position of said air-bubble removing unit on the side connected to said return pipe.

3. An automatic analyzer according to claim 2, wherein said air-bubble removing unit is provided with an air bleeding valve for expelling air bubbles accumulated in said air-bubble removing unit to the exterior.

4. An automatic analyzer according to claim 2, wherein said air-bubble removing unit has a structure with a top left open to an atmosphere.

5. An automatic analyzer according to claim 3, wherein a valve for draining the water in said constant temperature bath to the exterior is the same as said air bleeding valve provided on said air-bubble removing unit.

6. An automatic analyzer according to claim 5, further comprising a constant-temperature-bath water injecting valve disposed between said suction pipe and said return pipe and injecting the water into said constant temperature bath.

7. An automatic analyzer according to claim 6, further comprising a control mechanism for, when the constant temperature bath water is injected into said constant temperature bath by opening said constant-temperature-bath water injecting valve, controlling said valve to be opened and closed such that the constant temperature bath water is injected while said valve provided on said air-bubble removing unit is opened to drain the constant temperature bath water.

8. An automatic analyzer according to claim 7, wherein said control mechanism is so programmed as to automatically operate in accordance with a predetermined schedule.

* * * * *